(12) United States Patent
Quayle

(10) Patent No.: US 6,210,688 B1
(45) Date of Patent: Apr. 3, 2001

(54) USE OF POLYMERS AS FILM-FORMING BARRIER MATERIALS

(76) Inventor: Rachel Ann Quayle, Swaynes Jumps, Mill Lane, Willaston, S. Wirral, L64 1RN (GB)

( * ) Notice: Subject to any disclaimer, the term of this patent is extended or adjusted under 35 U.S.C. 154(b) by 0 days.

(21) Appl. No.: 08/750,219

(22) PCT Filed: Jun. 9, 1995

(86) PCT No.: PCT/GB95/01344

§ 371 Date: Feb. 14, 1997

§ 102(e) Date: Feb. 14, 1997

(87) PCT Pub. No.: WO95/33442

PCT Pub. Date: Dec. 14, 1995

(30) Foreign Application Priority Data

Jun. 9, 1994 (GB) .................................... 9411530

(51) Int. Cl.⁷ .............. A61K 9/70; A61K 7/46; A61L 15/42
(52) U.S. Cl. .............. 424/401; 424/443; 512/4; 428/905; 239/36
(58) Field of Search .............. 424/401, 61, 443, 424/448; 514/953; 512/1, 4; 428/905; 239/36

(56) References Cited

U.S. PATENT DOCUMENTS

| | | | |
|---|---|---|---|
| 1,300,592 | * 4/1919 | Essig . | |
| 3,544,364 | * 12/1970 | Rudner et al. . | |
| 3,577,516 | * 5/1971 | Gould et al. . | |
| 3,578,545 | * 5/1971 | Carson et al. . | |
| 3,590,118 | * 6/1971 | Conrady et al. . | |
| 3,655,129 | * 4/1972 | Seiner . | |
| 4,304,591 | * 12/1981 | Mueller et al. . | |
| 4,714,655 | * 12/1987 | Bordeldi et al. . | |
| 4,987,893 | * 1/1991 | Salamone et al. . | |
| 5,071,704 | * 12/1991 | Fischel-Ghodsian . | |

* cited by examiner

Primary Examiner—Edward J. Webman
(74) Attorney, Agent, or Firm—Anthony J. Casella; Gerald E. Hespos; Michael J. Porco

(57) ABSTRACT

The present invention is concerned with a method of forming a substantially non odorous barrier film, on human or animal skin on which a fragrance is to be applied, said method comprises applying a dermatologically inactive film-forming polymer to human or animal skin in a cosmetically acceptable carrier to form a substantially non odorous barrier film, on human or animal skin, onto which a fragrance is to be applied. A composition for use with the method of the invention is also disclosed.

15 Claims, No Drawings

USE OF POLYMERS AS FILM-FORMING BARRIER MATERIALS

The present invention relates to the use of polymers as film-forming barrier materials and more particularly to the use of these polymers to form substantially non odorous barrier films on the human or animal skin.

More particularly the present invention relates to the use of barrier films which are resistive to, for example, fragrances and/or insect repellents.

It is known that many perfumes smell differently in a bottle and on a wearers skin. Indeed the scent of a given perfume can even smell different on the same wearer with time. Thus the scent may change depending on, for example, what the wearer has eaten. This variation in smell is thought to be due to chemical reactions occurring on the skin between the fragrance and chemicals exuded therefrom.

This problem of scent variability, is a serious problem for both the wearer and the fragrance industry since a wearer can't predict with certainty how a given fragrance will smell and last on them. Furthermore they can't predict whether it will smell different if, for example, they are on medication or change their diet.

Further, it is known that the performance of insect repellents varies dependent upon the chemical reaction that can and does occur with a persons skin.

It is an aim of the present invention to provide a way of improving the likelihood of a given fragrance lasting a given time and emitting a given fragrance (smell).

It is also an aim of the present invention to provide a way of improving the performance of an insect repellent.

According to one aspect of the present invention there is provided the use of a barrier composition comprising a dermatologically inactive film-forming polymer in a cosmetically acceptable carrier therefore to form a substantially non odorous barrier film on human or animal skin.

By providing a substantially non-odorous fragrance resistive barrier film between the skin and the fragrance, chemical reactions between the skin and fragrance are prevented with the result that the smell emitted from the fragrance remains the same. Likewise the performance of an insect repellent can be improved by providing an insect repellent barrier film between the skin and the insect repellent.

It also has the added advantage that adverse reactions such as stinging, itching, rashes, discolouration, burning and dehydratation, which some people get when applying perfumes, aftershaves, insect repellents and the like may be alleviated.

According to a further aspect of the present invention there is provided a fragrance or insect repellent applicator kit comprising a fragrance or insect repellent and a barrier composition comprising a dermatologically inactive film-forming polymer and a cosmetically acceptable carrier therefore.

In order to produce a suitable barrier composition a suitable film-forming polymer must be chosen. For successful application they should be dermatologically inactive ie. no-irritant, non-sensitizing and non toxic, and preferably have a low permeability to the fluid e.g. perfume or insect repellent, to be applied, so that the perfume or insect repellent is kept away from the skin. When a fragrance is to be applied the film-forming polymer should be substantially aroma free so as not to overpower the smell of the fragrance which will be applied thereto.

Suitable polymers may include vinyl ether copolymers such as, for example, poly (ethyl vinyl ether)-co-(maleic anhydride), poly (methyl vinyl ether)-co-(maleic anhydride), poly (isobutyl vinyl ether)-co-(monoethyl maleate), poly (methyl vinyl ether)-co-(monoethyl maleate), and poly (methyl vinyl ether)-co-(monobutyl maleate); polyacrylates and methacrylates such as, for example, poly (butyl acrylate), poly (butyl acrylate)-co-(itaconic acid), poly (methyl methacrylate) to poly (n-butyl methacrylate) and acrylated/t-octyl propenamide copolymer; polyesters such as for example poly (vinyl stearate), poly (vinyl laureate), poly (vinyl stearate)-co-(itaconic acid) and poly (vinyl laureate)-co-(itaconic acid); polyfluorocarbons such as, for example, viton A a copolymer of vinylidene fluoride and hexafluoropropylene; and polysaccharides such as, for example, hydroxypropyl chitosan and quaternary hydroxypropyl chitosan.

The amount of polymer present in a barrier composition will depend on the molecular weight of the polymer since the end product must not be excessively viscous or it will not be possible to apply the barrier composition to the skin. Thus, the higher the molecular weight of the polymer, the lower its concentration in the barrier composition. Thus to avoid excessive viscosity, yet allow the barrier composition to contain sufficient polymer to be effective in forming a film-forming barrier, the polymer should preferably be present in amounts of from, for example, 3 to 25% by weight. However the precise values will depend on the molecular weight and the film forming properties of the polymer. Thus the higher the molecular weight of the polymer the lower the permissible maximum concentration.

The preferred polymers especially for fragrance usage, are poly (methyl vinyl ether-co-monbutyl maleate), acrylated/t-octyl propenamide copolymer and quaternary hydroxypropyl chitosan.

To enable easy application, the polymer should be dissolved or dispersed in an appropriate carrier and the chosen carrier will depend on the particular polymer.

Thus, for example, it is preferred to use approximately 20% wt/vol polymer where the polymer is a poly (methyl vinyl ether-co-monobutyl maleate), between about 4 to 6% wt/vol polymer where the polymer is an acrylated/t-octyl propenamide copolymer and about 6% wt/vol polymer where the polymer is a quaternary hydroxypropyl chitosan.

Thus where the polymer is a vinyl ether copolymer the carrier is preferably an alcohol such as for example ethanol.

Where the polymer is a methacrylate polymer the carrier is preferably an ethyl acetate.

Where the polymer is a polyacrylate the carrier is preferably an alcohol such as, for example, n-butyl alcohol or a ketone such as for example methyl ethyl ketone.

Where the polymer is a polyester the carrier is preferably acetone or ethylacetate.

Where the polymer is a polyfluorocarbon the solvent/carrier is preferably acetone and where the polymer is a quarternary hydroxypropyl chitosan the solvent/carrier is preferably industrial methylated spirit.

In order to give the polymer a degree of elasticity a plasticiser may be included. An example of a suitable plasticiser is diethylphthalate. This may be added in amounts of up to 1% wt/vol.

The composition may be applied by a spray, dab, drop and spread or wipe action and consequently the viscosity of the formulation will be altered accordingly. In order to achieve the desired consistency a surfactant may be included.

Other components may also be included as appropriate. Thus it may be necessary to neutralise the formulation and this will be achieved by altering the acidity or alkalinity as appropriate.

Thus, where the polymers are generally acidic due to the presence of for example for carboxyl groups, an alkaline neutralising agent such as a for example, potassium hydroxide may be added.

The polymeric film formed over the skin should also be resistant to degradation by the fluid to be applied e.g. the fragrance or perfume (and its carrier). Therefore polymers such as the polyacrylates and methacrylates, polyesters and polyfluorocarbons may be preferred as they are not significantly solubilised by lower alcohols.

In order for the fragrance, when applied to the film, to give off its aroma it must be warmed. The film should not therefore be so thick as to prevent body warmth initiating "evaporation" of the fragrance.

According to a further aspect of the present invention there is provided a method of improving the likelihood of a given fragrance or insect repellent lasting a given time and emitting a given smell, the method comprising the steps of:

i) applying a barrier composition comprising a dermatologically inactive film-forming polymer in a cosmetically acceptable carrier therefore to human or animal skin to form a substantially non-odorous fragrance or insect repellent resistive barrier film thereon, and ii) applying a fragrance or insect repellent onto said substantially non-odorous fragrance or insect repellent resistive barrier film.

Preferably the barrier composition is applied to the skin by a spray, dab, drop and spread or wipe action.

The invention will be further described, by way of example only, with reference to the following example compositions—% figures given as % wt/vol.

EXAMPLE 1

| | |
|---|---|
| Isoproponol | 79% |
| Butyl ester of PVA/MA copolymer - | 20% |
| Diethylphthalate - | 1% |

EXAMPLE 2

| | |
|---|---|
| Quarternary hydroxypropyl chitosan (LEXQUAT CH$_{TM}$) | 6% |
| Industrial methylated spirit | 94% |

EXAMPLE 3

| | |
|---|---|
| Acrylated/t-octyl propenamide copolymer (Dermacryl 79) | 4.400 |
| Dimethyl Pthalate | 0.176 |
| Potassium Hydroxide | 0.620 |
| Industrial Methylated Spirit 99% | TO 100% VOLUME |

EXAMPLE 4

| | |
|---|---|
| Acrylated/t-octyl propenamide copolymer (Dermacryl 79) | 5.400 |
| Dimethyl Pthalate | 0.216 |

-continued

| | |
|---|---|
| Potassium Hydroxide | 0.760 |
| Industrial Methylated Spirit 99% | TO 100% VOLUME |

What is claimed is:

1. A method of forming a substantially non odorous barrier film, on human or animal skin, on which a fragrance is to be applied such that chemical reactions between the skin and fragrance are prevented with the result that the smell emitted from the fragrance remains the same, said method comprising:

applying a dermatologically inactive film-forming polymer to human or animal skin in a cosmetically acceptable carrier to form the substantially non odorous barrier film; and after the non odorous barrier film has formed, applying the fragrance thereon.

2. A method according to claim 1 in which the dermatologically inactive film-forming polymer is selected from the group consisting vinyl ether copolymers, polyacrylates and methacrylates, polyesters, polyfluorocarbons and polysaccharides.

3. A method according to claim 1 in which the dermatologically inactive film-forming polymer is selected from the group consisting poly (methyl vinyl ether-co-monobutyl maleate), acrylated/t-octyl propenamide copolymer and quaternary hydroxypropyl chitosan.

4. A method according to claim 1 in which the polymer is present in an amount of from 3 to 35% by weight of the total composition.

5. A method according to claim 1 in which the cosmetically acceptable carrier is: an alcohol where the polymer is a vinyl ether copolymer; ethylacetate where the polymer is a methacrylate polymer; an alcohol or ketone where the polymer is a polyacrylate polymer; acetone or ethylacetate where the polymer is a polyester; acetone where the polymer is a polyfluorocarbon, and an alcohol where the polymer is a quaternary hydroxypropyl chitosan.

6. A method according to claim 1 which further comprises one or more of the group consisting of surfactant, plasticizer and a pH controlling agent.

7. A method of forming a substantially non odorous barrier film, on human or animal skin on which a fragrance is to be applied, said method comprising applying a dermatologically inactive film-forming polymer to human or animal skin in a cosmetically acceptable carrier to form a substantially non odorous barrier film, on human or animal skin, onto which a fragrance is then applied, wherein said dermatological inactive film-forming polymer is selected from the group consisting of poly (methyl vinyl ether-co-monobutyl maleate), acrylated/t-octyl propenamide copolymer and quaternary hydroxypropyl chitosan.

8. A method of forming a substantially non odorous barrier film, on human or animal skin on which a fragrance is to be applied, said method comprising applying a dermatologically inactive film-forming polymer on to human or animal skin in a cosmetically acceptable carrier to form a substantially non odorous barrier film, on human or animal skin, onto which the fragrance is applied, and wherein said dermatologically inactive film-forming polymer is selected from the group consisting of poly (methyl vinyl ether-co-monobutyl maleate), acrylated/t-octyl propenamide copolymer and quaternary hydroxypropyl chitosan.

9. A method of forming a substantially non odorous barrier film, on human or animal skin on which a fragrance is to be applied, as defined in claim 8, said method comprising spraying a dermatologically inactive film-forming polymer onto human or animal skin in a cosmetically acceptable carrier to form a substantially non odorous barrier film, on human or animal skin, onto which a fragrance is then applied.

10. A method of forming a substantially non odorous barrier film, on human or animal skin on which a fragrance is to be applied, as defined in claim 8, said method comprising dabbing a dermatologically inactive film-forming polymer onto human or animal skin in a cosmetically acceptable carrier to form a substantially non odorous barrier film, on human or animal skin, onto which a fragrance is then applied.

11. A method of forming a substantially non odorous barrier film, on human or animal skin on which a fragrance is to be applied, as defined in claim 8, said method comprising dropping a dermatologically inactive film-forming polymer onto human or animal skin in a cosmetically acceptable carrier to form a substantially non odorous barrier film, on human or animal skin, onto which a fragrance is then applied.

12. A method of forming a substantially non odorous barrier film, on human or animal skin on which a fragrance is to be applied, as defined in claim 8, said method comprising spreading a dermatologically inactive film-forming polymer onto human or animal skin in a cosmetically acceptable carrier to form a substantially non odorous barrier film, on human or animal skin, onto which a fragrance is then applied.

13. A method of forming a substantially non odorous barrier film, on human or animal skin on which a fragrance is to be applied, said method comprising applying a dermatological inactive film-forming polymer to human or animal skin in a cosmetically acceptable carrier to form a substantially non odorous barrier film, on human or animal skin, onto which a fragrance is then applied, wherein said dermatological inactive film-forming polymer is selected from the group consisting of poly (methyl vinyl ether-co-monobutyl maleate), acrylated/t-octyl propenamide copolymer and quaternary hydroxypropyl chitosan and the cosmetically acceptable carrier is: an alcohol where the polymer is a poly (methyl vinyl ether-co-monobutyl maleate); an alcohol or ketone where the polymer is a acrylated/t-octyl propenamide copolymer; acetone or ethylacetate where the polymer is a polyester; and an alcohol where the polymer is a quaternary hydroxypropyl chitosan.

14. A method of forming a substantially non odorous barrier film, on human or animal skin on which a fragrance is to be applied, said method comprising applying a dermatological inactive film-forming polymer to human or animal skin in a cosmetically acceptable carrier to form a substantially non odorous barrier film, on human or animal skin, onto which a fragrance is then applied, wherein said dermatological inactive film-forming polymer is selected from the group consisting of poly (methyl vinyl ether-co-monobutyl maleate), acrylated/t-octyl propenamide copolymer and quaternary hydroxypropyl chitosan, and the cosmetically acceptable carrier is: an alcohol where the polymer is a poly (methyl vinyl ether-co-monobutyl maleate); an alcohol or ketone where the polymer is an acrylated/t-octyl propenamide copolymer; and an alcohol where the polymer is a quaternary hydroxypropyl chitosan.

15. A method of forming a substantially non odorous barrier film, on human or animal skin on which a fragrance is to be applied, said method comprising applying a dermatological inactive film-forming polymer to human or animal skin in a cosmetically acceptable carrier to form a substantially non odorous barrier film, on human or animal skin, onto which a fragrance is then applied, wherein said cosmetically acceptable carrier is: an alcohol where the polymer is a poly (methyl vinyl ether-co-monobutyl maleate); an alcohol or ketone where the polymer is an acrylated/t-octyl propenamide copolymer; acetone or ethylacetate where the polymer is a polyester; and an alcohol where the polymer is a quaternary hydroxypropyl chitosan.

* * * * *